United States Patent [19]
Dechene et al.

[11] Patent Number: 5,095,275
[45] Date of Patent: Mar. 10, 1992

[54] LONG TERM PARTICLE MONITORING

[75] Inventors: Ronald L. Dechene, Boxford; Robert E. Newton, Tewksbury; Russell S. Girgenti, South Hamilton, all of Mass.

[73] Assignee: Auburn International, Inc., Danvers, Mass.

[21] Appl. No.: 555,306

[22] Filed: Jul. 19, 1990

[51] Int. Cl.$^5$ .......................................... G01N 27/60
[52] U.S. Cl. ................................ 324/454; 324/71.1
[58] Field of Search ............... 324/454, 71.1, 452; 73/866.5, 861.04, 28.01

[56] References Cited
U.S. PATENT DOCUMENTS

| | | | |
|---|---|---|---|
| 2,209,614 | 7/1940 | Rowley | 73/28.01 |
| 3,699,348 | 10/1972 | Hocherl | 73/864.24 |
| 4,714,890 | 12/1987 | Dechene et al. | 324/71.1 |
| 4,904,944 | 2/1990 | Dechene et al. | 324/71.1 |
| 4,961,147 | 10/1990 | Moore | 324/71.1 |

Primary Examiner—Kenneth A. Wieder
Assistant Examiner—Maura K. Regan
Attorney, Agent, or Firm—Jerry Cohen

[57] ABSTRACT

Monitoring apparatus (10) of particles in a gas stream comprising a probe (12) and circuit (14) for detecting electrical activity of the probe and an actuator (20) for insertion and retraction of the probe into and out of the stream, the circuit providing periodic measurement of the retracted probe and self-adjustment to compensate for changing probe characteristics. The apparatus also provided probe cleaning and protection means (30, 32, 34, 36), which work in interaction with the self-check instrumentation. The self-check tests include baseline, gain and sensitivity monitoring.

7 Claims, 3 Drawing Sheets

LONG TERM PARTICLE MONITORING

BACKGROUND OF THE INVENTION

The present invention relates to instrumentation for long term monitoring of fine particles in gas streams, such as stack emissions of combustion systems and industrial equipment generating soot, ash, dusts, granules and other fine particles.

The means for such monitoring include optical, radioactive, acoustic and electric transducers. Each has its unique merits and drawbacks. There are also a number of common drawbacks. Some of the common drawbacks include drift of transducers and circuits. Off-line calibration is impractical in many usages.

It is an object of the invention to provide an electric transducer and circuit which reliably monitors stream conditions over a long term.

SUMMARY OF THE INVENTION

In accordance with the present invention a triboelectric system is utilized. Triboelectric measurement per se is described e.g., in U.S. Pat. No. 4,714,890, granted Dec. 22, 1987, U.S. Pat. No. 4,619,145, granted Oct. 28, 1986, U.S. Pat. No. 4,774,453, granted Sept. 27, 1988, Ser. No. 07/135,661, filed Dec. 21, 1987, and U.S. Pat. No. 4,631,482, granted Dec. 23, 1986. The teachings of which are incorporated herein by reference.

The system of the present invention utilizes a probe in the gas stream and means for inserting the probe into the gas stream and retracting the probe completely from the stream. The triboelectric measurement circuit imposes a test routine on the retracted probe and measures, and compensates for, drift in electrical response of the probe and of the circuit itself. The system can be configured for periodic probe withdrawal for such correction once a day or at any interval, usually depending on the conditions of the monitored gas stream and in some instances at hour intervals or integral numbers of hours.

Through baseline adjustment—usually "rezeroing-"—the invention corrects for drift introduced by several causes including among others, coating of the probe by fine solid particles of the gas stream and resultant reduction in sensitivity, possible bridging of the probe to ground and resultant localized battery effects and/or unusual behavior of suspended fine particles unique to the particular environment and/or time frame of measurement.

The invention also comprises a secondary correction through periodic electrode cleaning. The cleaning is carried out by a mechanical cleaning means such as wiper seal and a circumferential gas jet imposed during retraction and/or insertion of the electrode. This is primarily to purge the insulator interface between the probe and assembly face, and eject any dust removed during retraction with air or other gas, apart from the air cylinder connections. The circumferential gas jet also acts to prevent bridge formation with the probe inserted. Leakage circuit paths are minimized by using a tower structure extending out from a bounding wall (e.g., duct wall) of the gas stream with a probe entrance/exit (with the mechanical cleaning means) on a tower spaced out from the wall. The withdrawn probe is held in the tower. The tower structure also provides stable support for the probe when extended. A short length actuator system is used for probe insertion-retraction. The short length actuator system comprises a probe extension and a parallel linear actuator carrying the extension.

A system of contacts at end limits of probe/extension movement provides interconnection of the probe and measuring circuit. During probe movement, there is no connection of probe and measuring circuit. This provides a practical, safe approach to combined in-line measurement/correction with use of a single circuitry.

Other objects, features and advantages will be apparent from the following detailed description of preferred embodiments taken in conjunction with the accompanying drawing in which:

DETAILED DESCRIPTION OF PREFERRED EMBODIMENTS

Figure 1:
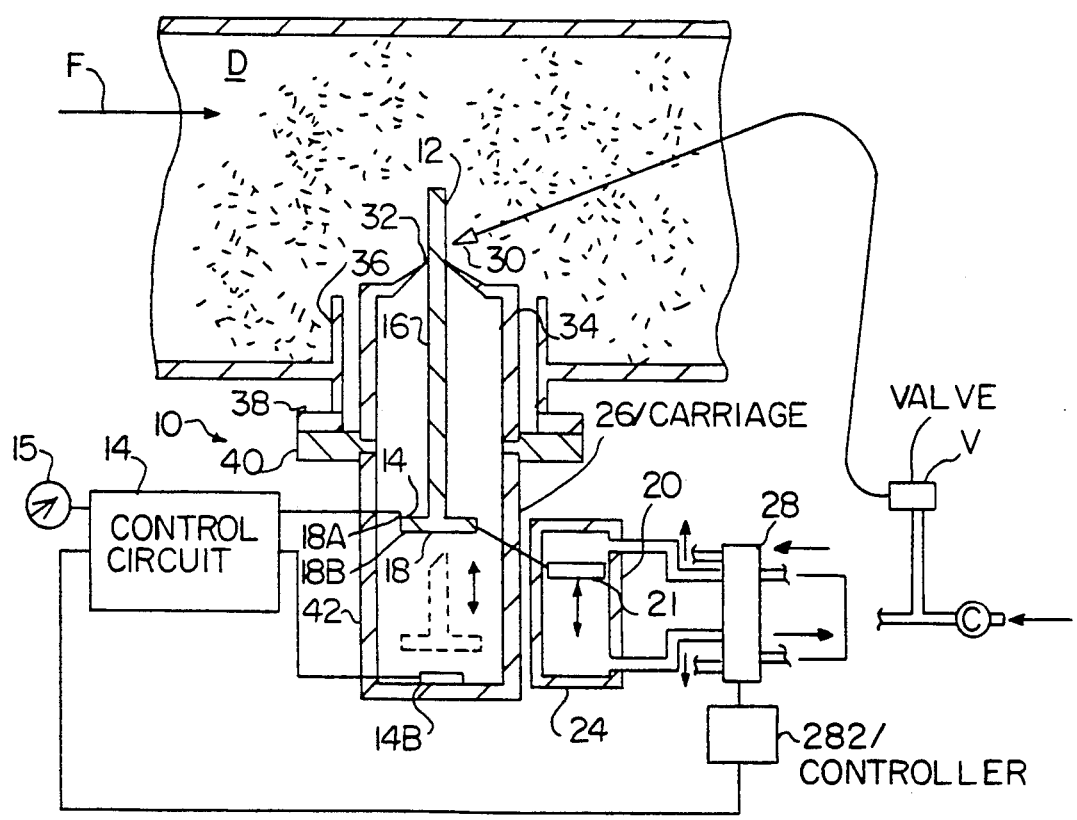
FIG. 1 is a schematic diagram of mechanical elements of a preferred embodiment of the invention.

In FIG. 1 there is shown a volume to be monitored such as a duct D carrying gas borne fine particles (dusts) with a general flow direction F. The volume may be part of a combustion exhaust or other industrial effluent duct. The measuring system 10 comprises a rod probe form of triboelectric electrode 12 and electrical measuring circuit 14 with one or more output devices 15, e.g., display device, recorder and/or process controller. The measuring circuit comprises the elements shown e.g., in the above cited U.S. patents for triboelectric or like measurements. The first listed one is preferred. The probe has an extension 16 terminating in a piston end 18 with contact sets 18A and 18B on top and bottom sides thereof for engaging corresponding contact sets 14A and 14B connected to the measuring circuit. A band cylinder pneumatic actuator 20, with a drive connection 22 from an internal component 24 to piston 18, is operable from a compressor C and a solenoid operated valve 28 with controller 282 which is also interconnected to control circuit 14. An air jet 30 is also fed from the compressor directly or via the valve V.

The probe is usually interposed into the gas stream such that accurate triboelectric readings of the particulate matter are detected. This will be termed "sensor effective" contact as to the probe and gas stream. The probe 12 is retractable from its measuring position of sensor effective contact as shown in FIG. 1 past a wiper seal 32 to a fully retracted position within an enclosing tower 34 (which is in turn surrounded by a spaced tubular dust shield 36). A flange system 38/40 and a cylinder 42 for a probe base 18 completes the enclosure of the retracted probe. Upon full retraction the contacts 18B engage contacts 14B. During retraction jet 30 blows away particle build-up at the probe/seal wiping interface. Jet 30 is preferrably of an annular form.

The probe drive system 20 comprises a piston 21, a cylinder 24, a carriage 26 and an air control solenoid operated valve 28 with controlled 282 is of a type more fully described in U.S. Pat. Nos. 4,545,290 and 4,724,744.

Figure 2:
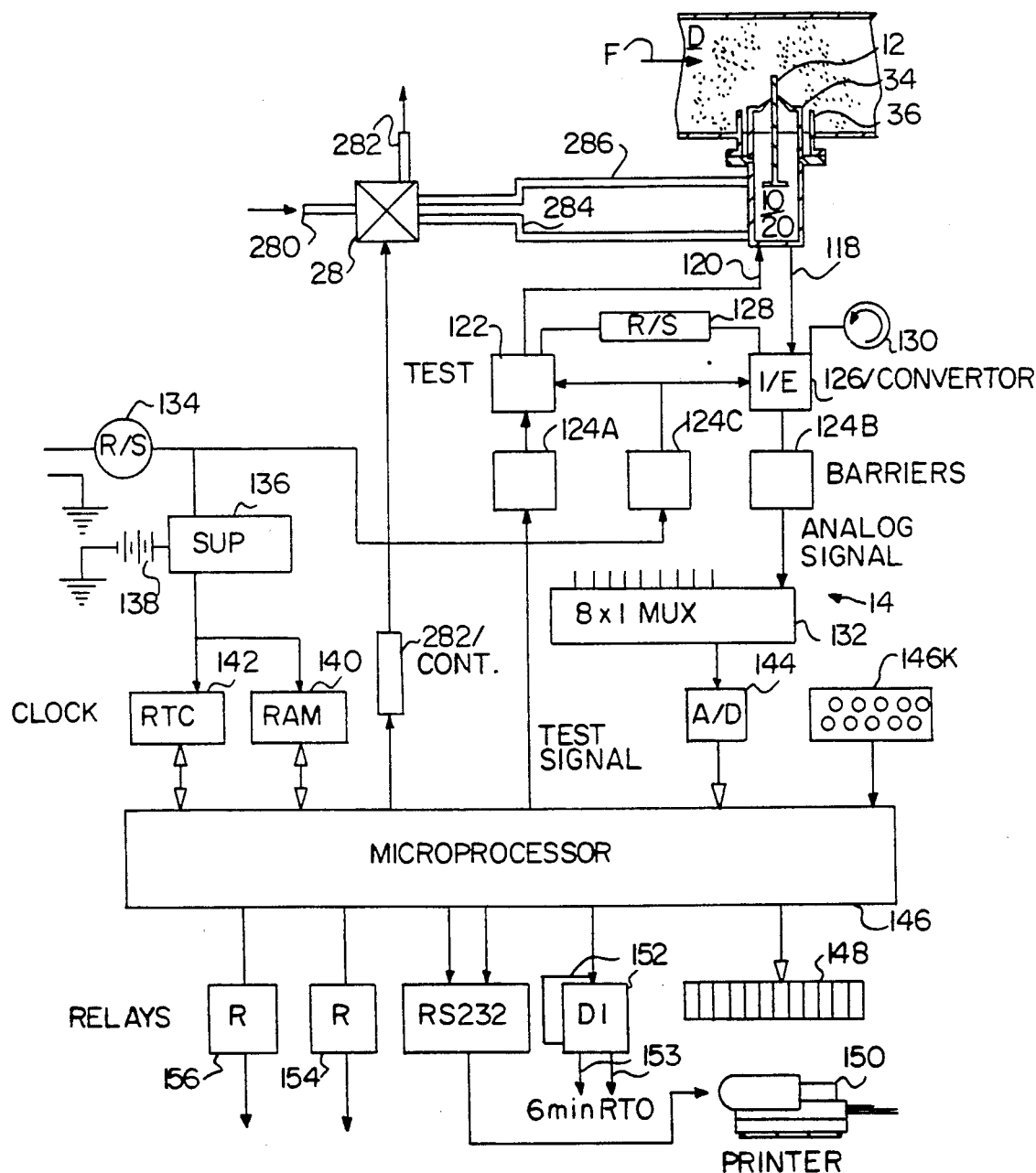
FIG. 2 is a block diagram of circuitry of the FIG. 1 embodiment.

In FIG. 2 there is shown duct D. Inserted therein is the retractable probe and surrounding elements 34, 36 described above. The probe is insertable from and retractable into assembly 10/20 described above. As stated above, valve 28 controls gas input and exhaust to air drive 20 with air inlet at 280, exhaust at 282 and air feed lines 284, 286. Valve 28 is directed by controller 282 which is in turn connected to a microprocessor portion 146 of the control circuit 14.

The control circuit is connected to contacts of assembly 10 (as described above re FIG. 1) and is connected with a probe current probe cable 118 and test current cable 120. The test cable 120 and probe are connected to the microprocessor via these elements: (a) test cable to test circuit 122 and (b) probe cable via current to voltage converter 126 and analog to digital converter 144. The series path includes intrinsically safe barrier means 124a, 124b, 124c [which comprise, preferrably, a redundant Zener diode and fuse. Test circuit 122 also communicates with converter 126, and they are connected by a range switch 120 (further connectable to test circuit 222) and a gain control potentimeter 130. A multiplex (MUX) system 132 enables similar analog signals of other probes to be served by the same control circuit.

A power supply 134 further is controllably connected to a power supervisor 136 and a battery 138. The power supervisor 136 uninterruptably supplies a RAM 140 and real time clock 142. The RAM and real time clock are each connected to the microprocessor 146V. The microprocessor is further connected to a key pad 146, Liquid crystal display 248, RS232 interfaces, which may typically connect to a printer 150, digital to current (4-20 mA) converters 152 providing averaged and/or real time outputs 153. The microprocessor is further connected to relay means 154 and 156 acting as prewarning and warning means.

From the detailed explanation of the operation of this invention it will be seen that the combined cleaning and recalibrating of baseline are central advantages herein provided. Reliable and continuous in line data on gas stream particulat content are provided over an indefinite time period by the expedient of the self cleaning feature of this device produced both continuously and in conjunction with the rezeroing cycle.

OPERATION

Figure 3:
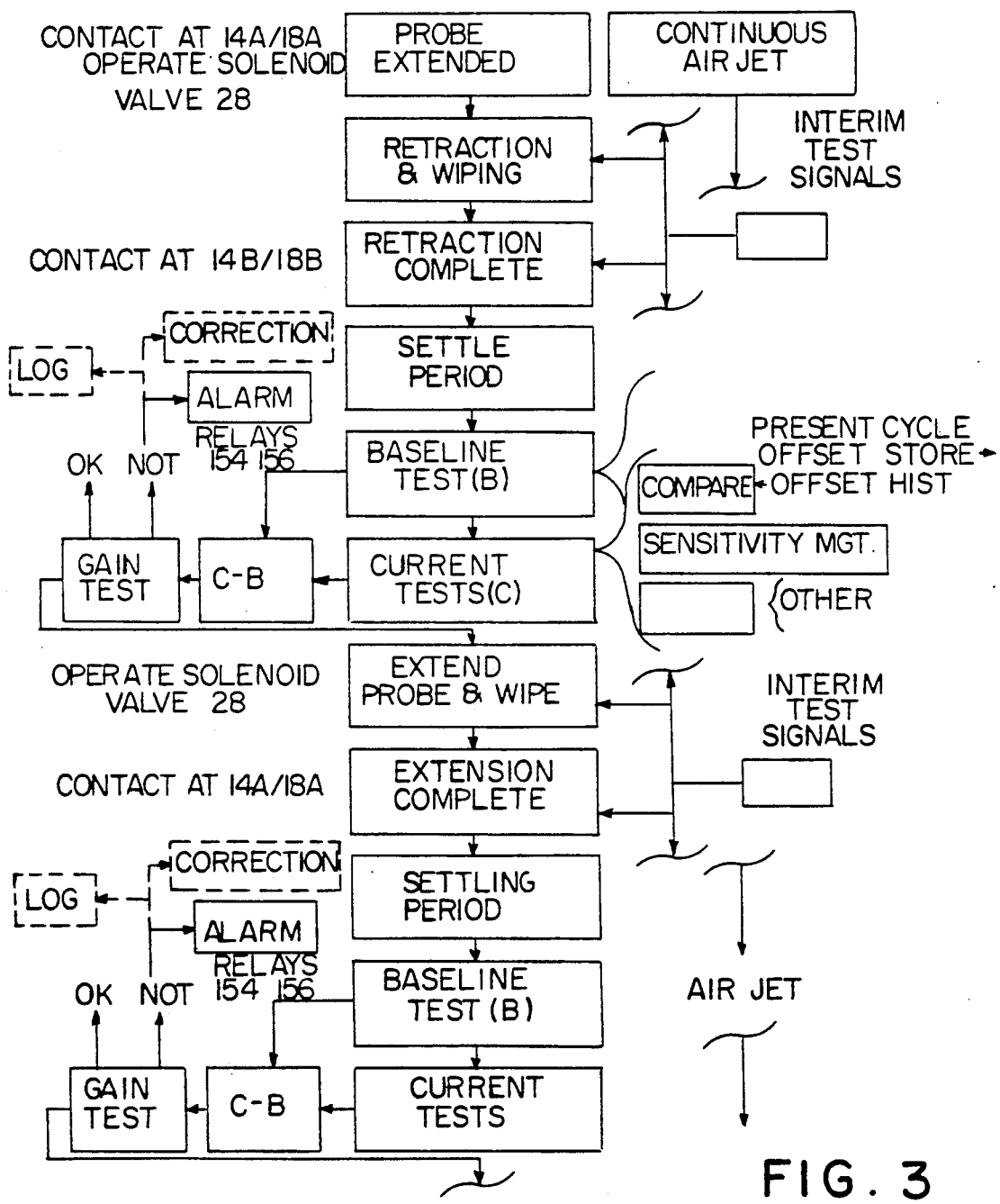
FIG. 3 is a block diagram of control functions.

The preferred operation of the device illustrated by the block diagram of FIG. 3 is as follows:

The circuit 14 initiates an auto base line adjustment to zero (the calibration sequence) at least once each twenty four hours. The period may be reduced in one hour increments to a frequency of about once per hour. The sequence is as follows:

1. The circuit 14 energizes four way solenoid valve 28 which applies air to the inboard end of the sensor cylinder 20 (FIGS. 1/2) causing the probe assembly 12-16-18 (FIG. 1) to retract from the duct D.

2. As the probe retracts, any material accumulation such as dust on the probe surface is removed and the probe is isolated from triboelectric activity in the duct.

3. When fully retracted, the probe makes simultaneous contact with output signal and test signal cables from the circuit 14 via contacts 14B, 18B.

4. After a settling period (due to the triboelectric effect on the probe during retraction), the measuring circuit outputs a baseline level test current and records any offset.

5. Next, the circuit outputs a series of test current steps until a given signal level is achieved.

6. The electronics subtracts the baseline or "zero" offset and then determines the conversion gain setting of the electronics. If it is not the same as previously recorded an alarm (low level) is generated since tampering or a malfunction is indicated.

7. Then, controller 282 deenergizes the solenoid valve 28 which exhausts the board side of cylinder 20 and pressurizes the other side to thereby extend the probe 12 into the duct. At the fully extended position, the probe again makes contact with both the output and test signal cables via contacts 18A, 14A.

8. The measuring circuit 14 momentarily outputs a short high level test signal to verify that the probe has fully extended. After a short settling delay, the system returns to normal operation.

The probe can make contact with the test and output signal cables only at the fully extended or retracted positions. Thus, if a test signal is applied without a resulting output signal at either end of travel, a probe malfunction is indicated.

Baseline setting establishes a zero offset and stores it for correction until the next retraction and baseline determination sequence. A malfunction is indicated if the baseline exceeds 5% of full scale which initiates a low level alarm. The apparatus can also be constructed to trigger a corrective action and/or direct data logging of the incident.

The current test can be a single suite of tests or a repeated series with averaging or other statistical manipulation. Each such suite can include sensitivity and gain testing.

A sensitivity setting is measured and a prompt appears on computer display asking the operator to enter the numerical (dial) sensitivity control setting.

The operator enters the control setting. The measured and entered settings are compared to verify proper circuit operation. If the two settings do not agree within +/− 10% an error is indicated and must be corrected. The comparison is initially used to insure proper operation, however, the measured sensitivity value and baseline zero correction is applied to all data until the next auto calibration sequence is accomplished.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. System for monitoring concentrations of particles in a moving gas stream comprising:
   (a) a probe for intercepting gas borne particles for triboelectric interaction;
   (b) a probe-extension/retraction assembly for periodically extending the probe into the stream and retracting the probe;
   (c) contact means for contacting the probe at limits of insertion/retraction movement;
   (d) measuring means for detecting electrical activity of the probe via said contact means and comprising means for:
      (d1) testing the electrical response of the retracted probe, and
      (d2) said measuring circuit means constructed to respond to offset drift in probe response for use when the probe is next inserted.

2. System in accordance with claim 1 and further comprising means for cleaning surface contamination of the probe during retraction movement.

3. System in accordance with claim 2 wherein the cleaning means comprises a probe wiping seal.

4. System in accordance with claim 3 and further comprising gas jet flowing means directed at the wiping seal.

5. System in accordance with claim 1 wherein the insertion/retraction means comprises a linear extension of the probe and linear actuator arranged in parallel with the extension and carrying the extension.

6. System in accordance with claim 5 wherein insertion/retraction means comprises a tower extending from a bounding wall of the stream and having a tower top entrance/exit for the probe.

7. System in accordance with claim 1 wherein said means for detecting electrical activity of the probe includes means for amplifying and extracting a current signal from triboelectric events at the probe and measuring said current signal in the absence of triboelectric events as produced by test current input and the system further includes means to establish a zero baseline in each retraction and compare the same with one or more baselines of one or more prior retractions.

* * * * *